United States Patent
Avallin et al.

(10) Patent No.: US 10,227,377 B2
(45) Date of Patent: Mar. 12, 2019

(54) ARRANGEMENT FOR A COLUMN, A METHOD FOR SUBSTITUTING A TUBULAR HOUSING IN SUCH AN ARRANGEMENT FOR A COLUMN AND A METHOD FOR CONDUCTING PEPTIDE AND/OR OLIGONUCLEOTIDE SYNTHESIS IN A COLUMN

(71) Applicant: GE Healthcare Bio-Sciences AB, Uppsala (SE)

(72) Inventors: Johan Avallin, Uppsala (SE); Per Denker, Bromma (SE); Carina Andersson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 305 days.

(21) Appl. No.: 14/904,080

(22) PCT Filed: Jul. 8, 2014

(86) PCT No.: PCT/SE2014/050871
§ 371 (c)(1),
(2) Date: Jan. 8, 2016

(87) PCT Pub. No.: WO2015/005858
PCT Pub. Date: Jan. 15, 2015

(65) Prior Publication Data
US 2016/0152660 A1 Jun. 2, 2016

Related U.S. Application Data

(60) Provisional application No. 61/843,978, filed on Jul. 9, 2013.

(51) Int. Cl.
*G01N 1/00* (2006.01)
*C07K 1/02* (2006.01)
(Continued)

(52) U.S. Cl.
CPC ........... *C07K 1/02* (2013.01); *B01D 15/22* (2013.01); *B01J 19/2415* (2013.01); *C07H 1/06* (2013.01);
(Continued)

(58) Field of Classification Search
CPC .... G01N 30/02; G01N 30/60; G01N 30/6021; G01N 30/6047
See application file for complete search history.

(56) References Cited

U.S. PATENT DOCUMENTS

| 5,641,459 | A | 6/1997 | Holmberg | |
|---|---|---|---|---|
| 7,686,953 | B2 * | 3/2010 | Bailey | B01D 15/22 210/198.2 |

(Continued)

FOREIGN PATENT DOCUMENTS

| EP | 3019860 A | 5/2015 |
|---|---|---|
| JP | 07089983 A | 4/1995 |

(Continued)

OTHER PUBLICATIONS

International Search Report and Written Opinion issued in connection with corresponding PCT application PCT/SE2014/050871 dated Oct. 13, 2014.

(Continued)

*Primary Examiner* — Jyoti Nagpaul
(74) *Attorney, Agent, or Firm* — Wood IP LLC

(57) ABSTRACT

An arrangement for a column comprising a stand provided with a platform adapted to receive a second end of a tubular housing and for supporting the arrangement on a floor, a first end unit removably connected to a first end of the tubular housing, an adaptor assembly movable within said tubular housing and an adaptor rod connected to said adaptor assembly, which adaptor rod is arranged to extend through an opening in the first end unit. A frame is connected to the (Continued)

first end unit, which frame and first end unit can be lifted and lowered in a substantially vertical direction, so that the tubular housing may be removed and substituted for another tubular housing with different dimensions in relation to the removed tubular housing when the frame and first end unit are lifted.

10 Claims, 6 Drawing Sheets

(51) Int. Cl.
*B01D 15/22* (2006.01)
*G01N 30/60* (2006.01)
*B01J 19/24* (2006.01)
*C07H 1/06* (2006.01)
*C07H 21/00* (2006.01)
*C07K 1/16* (2006.01)
*G01N 30/88* (2006.01)

(52) U.S. Cl.
CPC ............... *C07H 21/00* (2013.01); *C07K 1/16* (2013.01); *G01N 30/6021* (2013.01); *G01N 30/6047* (2013.01); *G01N 30/6017* (2013.01); *G01N 2030/8831* (2013.01)

(56) References Cited

U.S. PATENT DOCUMENTS

| | | |
|---|---|---|
| 2006/0091052 A1 | 5/2006 | Uselis et al. |
| 2011/0120951 A1 | 5/2011 | Hampton et al. |

FOREIGN PATENT DOCUMENTS

| | | |
|---|---|---|
| JP | 11512085 A | 10/1999 |
| JP | 2010513873 A | 4/2010 |
| JP | 2011-215008 A | 10/2011 |
| WO | 2008076830 A2 | 6/2008 |
| WO | 2009/105216 A2 | 8/2009 |
| WO | 2011049312 A2 | 4/2011 |
| WO | 2011073067 A1 | 6/2011 |
| WO | 2011/162678 A1 | 12/2011 |
| WO | WO2011162678 A2 * | 12/2011 |
| WO | 2013191641 A1 | 12/2013 |
| WO | 2015/005858 A1 | 1/2015 |

OTHER PUBLICATIONS

International Preliminary Report on Patentability Received for PCT Patent Application No. PCT/SE2014/050871, dated Jan. 12, 2016, 7 Pages.
Extended European Search Report Received for European Patent Application No. 14823662.3, dated Jan. 27, 2017, 6 pages.
Japan Notice of Preliminary Rejection for Japanese Patent Application No. 2016-525328, dated Jul. 10, 2018, 4 pages.

* cited by examiner

ARRANGEMENT FOR A COLUMN, A METHOD FOR SUBSTITUTING A TUBULAR HOUSING IN SUCH AN ARRANGEMENT FOR A COLUMN AND A METHOD FOR CONDUCTING PEPTIDE AND/OR OLIGONUCLEOTIDE SYNTHESIS IN A COLUMN

FIELD OF THE INVENTION

Embodiments of the invention relate to peptide and/or oligonucleotide synthesis.

BACKGROUND OF THE INVENTION

The chromatography technique is widely used in different forms for separating chemical and biological substances and there are many applications in compound preparation, purification and analysis. Liquid chromatography is of particular importance in the pharmaceutical and biological industries for the preparation, purification and analysis of proteins, peptides and nucleic acids.

A typical liquid chromatography apparatus has an upright housing in which a bed of packing material, which is usually in particulate in nature and consists of a porous medium, rests against a permeable retaining layer. A liquid mobile phase enters through an inlet, for example at the end of an adaptor rod which has an elongated extension within the column. The liquid mobile phase thereafter enters an adaptor assembly comprising a distributor plate which distributes the liquid mobile phase through a porous, perforated filter, mesh, frit or net, arranged on the adaptor plate. The liquid mobile phase thereafter moves through the bed of packing material and is finally removed via an outlet, typically through a second filter, mesh, frit or net and a second distributor plate.

Columns used in liquid chromatography typically comprise a tubular housing enclosing the porous chromatography medium through which the carrier liquid or mobile phase flows, with separation of substances or analytes taking place between the mobile phase and solid phase of the porous medium. Typically, the porous medium is enclosed in the column as a packed bed, generally formed by consolidating a suspension of discrete particles, known as slurry that is pumped, poured or sucked into the column, usually from a bore or nozzle located at the tubular housing or at one end of the column.

Conventional distribution systems for use in liquid chromatography comprise a distributor plate which comprises channels arranged in a pattern to substantially uniform distribute the fluid over the plate. The distributor plate is perforated with holes or openings which lead the fluid from the channels and uniformly into the packed bed.

The backing plate or the lowermost, second end unit of the chromatography columns generally acts as a support for the column, being itself supported on legs or some other stand arrangement positioned on the floor which allows clearance for an outlet pipe work projecting beneath the column.

Such known chromatography apparatuses are provided with a column having a fixed high and diameter and thus a fixed volume. Depending on the type of proteins, peptides and nucleic acids which should be used for preparation, purification and analysis different sizes of chromatography apparatus will be used in order to achieve a proper result. Therefore, most of the pharmaceutical and biological industries are equipped with a large number of chromatography apparatuses of different sizes.

In peptide and oligonucleotide synthesis different types of methods, machines and equipments may be used. An oligonucleotide is a macromolecule comprising a sequence of nucleosides, each of which includes a sugar and a base. Each nucleoside is separated from adjacent nucleosides with an internucleoside linkage, which effectively serves to bond the nucleosides together. A number of different sugars and bases can be used. The internucleoside linkage is most commonly a phosphate, which may be substituted with a variety of substitutents at a non-bridging oxygen atom.

One method used for synthesizing oligonucleotides is the phosphoramidite method. To produce a large number of oligonucleotide molecules with this method, a solid support is provided in a reaction vessel and a large number of DMT-protected nucleosides are fixed to the support. In a first step, a deprotectant acting through a detritylation mechanism, is added to remove the DMT from nucleoside, and thus to "deprotect" that one hydroxyl. As a result, the last nucleoside in the sequence has one hydroxyl that is ready to receive a next amidite. In a second step, nucleoside phosphoramidites (hereafter "amidites") dissolved in a solvent such as acetonitrile (ACN), are introduced into the vessel. An activator, is also introduced into the vessel with the amidites. The phosphorus in the amidites bonds with the oxygen in the hydroxyl, thus providing support-bound nucleotides. After the support-bound nucleotides are formed, excess amidites are flushed from the vessel with ACN.

In a third step, an oxidizing agent is added to convert the trivalent phosphorous to pentavalent. After the oxidizing agent is flushed, a capping agent is added in a fourth step to block all the unprotected hydroxyls from reacting with amidites introduced at a later stage. Thereafter, ACN is again introduced to flush out the capping agent.

These steps are repeated a number of times to produce growing, oligonucleotide chains from support-bound nucleosides. Each of the chains should have an identical repeating sequence of nucleosides.

This method is however time consuming and the materials that are used, particularly the amidites, are expensive and require special handling and disposal after being used.

In larger quantities, the production of oligonucleotides raises several concerns. Because of the interest in using synthesized oligonucleotides for human use, the oligonucleotides have a high degree of homogeneity. Meanwhile, competing concerns affect the efficient use of materials, particularly the amidites and the ACN. While an excess amount of amidites is needed to ensure that as many as possible of the nascent oligonucleotides react with newly introduced amidites, the quantity of amidites introduced into the vessel should not be too excessive and wasteful. It is also desirable to reduce the amount of ACN that is used, while still flushing out, or at least diluting, leftover amidites as much as possible. If the flushing is insufficient, leftover amidites in the vessel or in various conduits leading to the column can produce nonhomogeneous sequences.

A known machine uses a flow-through design in which various conduits, pumps, and valves are constantly filled with liquid. Liquid introduced into a column displaces previously introduced liquid. This flow-through system is distinguished from a "batch" system in which liquids are introduced into a reaction vessel, the introduced liquids are flushed out, and the steps of introducing and flushing liquids is repeated. In such a batch device, the liquids are provided to the vessel by gas pressure and not with pumps. This approach can be used because a batch process has gaps in the flow of fluid. To regulate the amounts of the liquids that are provided to the column, each of the pumps is initially calibrated. During operation, the pumps are activated a certain period of time to provide the desired quantities of liquid. Periodically, the pumps need to be rechecked and recalibrated to avoid problems that can result from drifting in the pump.

U.S. Pat. No. 5,641,459 shows a machine for synthesizing oligonucleotides provided with a control system which control the volumes of liquid that are introduced during operation. The control system avoids the need to recalibrate due to drifting because valves are regulated during operation. By using three-way valves in which one, both, or neither of the inlet ports can be open at one time, different capping agents can be mixed together in the valve; the activator and amidites also can be simultaneously introduced and mixed. The valves in the modules are also coupled to receive a flushing agent.

Oligonucleotide and peptide synthesis use large volumes of expensive reagents and solvents. The bed volume increases during the synthesis, partly due to swelling solid support and partly due to synthesized product. When synthesis is performed in a vessel with a fixed volume the distribution of the reagent over the whole accessible area for neuclotide/peptide binding may be unfavourable. Also, an access of solvent which dilutes the reagents during synthesis may affect the synthesis performance and reliability, since low concentration means slower kinetics. The synthesis may take a few hours or a week long depending on the amount and volume of the product to be synthesized. Therefore, any manual handling throughout the synthesis process should be avoided.

SUMMARY OF THE INVENTION

Notwithstanding the existence of such prior art columns described above, there is a need to increase the flexibility of a column and to reduce the number of columns of different sizes used by the pharmaceutical and biological industries. Also, notwithstanding the existence of prior art machines for synthesizing oligonucleotides and peptides, there is a need to reduce any manual handling throughout the synthesis process.

An objective problem to be solved by an embodiment of the present invention is to increase the flexibility of a column.

Another objective problem to be solved by an embodiment of the present invention is to reduce the number of columns of different sizes when performing preparation, purification and analysis of different substances.

Still another objective problem to be solved by an embodiment of the present invention is to reduce any manual handling throughout the process for synthesizing peptides and/or oligonucleotides.

These objects above are achieved by an arrangement for a column, a method for substituting a tubular housing in an arrangement for a column, a method for conducting peptide and/or oligonucleotide synthesis in a column, a computer program for controlling peptide and/or oligonucleotide synthesis in a column; and a computer program product comprising program code, as set forth herein.

The arrangement for the column, the method for conducting peptide and/or oligonucleotide synthesis in a column, the computer program for controlling peptide and/or oligonucleotide synthesis in a column and the computer program product comprising program code increase the flexibility of a column and reduce the number of columns of different sizes when performing preparation, purification and analysis of different substances. Also, manual handling throughout the process for synthesizing peptides and/or oligonucleotides is reduced.

Controlling of the adjustable adaptor in the head space above the bed avoids any manual handling throughout the synthesis run, which may take a few hours or a week long.

The programmed motorized automated adaptor movement and the distribution system enable the optimized automated synthesis concept with an even distribution of reagents and make it possible to minimize the dilution of the reagents and also to minimize the usage of expensive solvents.

The combination of the arrangement for the column for peptide and/or oligonucleotide synthesis with a programmed motorized automated adaptor solves the automation of the synthesis. Using separate adaptable cassette inserts or exchangeable tubes and distributors with the size and dimension needed for the synthesis increase the flexibility of the arrangement and reduce the number of apparatuses of different sizes when performing preparation, purification and synthesis of different substances.

An embodiment of the present invention accordingly comprises an arrangement for a column, a method for conducting peptide and/or oligonucleotide synthesis in a column, a computer program for controlling peptide and/or oligonucleotide synthesis in a column and a computer program product comprising program code that will be exemplified in the description set forth hereinafter and the scope of the invention will be indicated in the claims.

BRIEF DESCRIPTION OF THE DRAWINGS

Further aspects, advantages and features of the invention can be derived from the following detailed description of an embodiment of the invention, with reference to the drawings.

DETAILED DESCRIPTION

Figure 1:
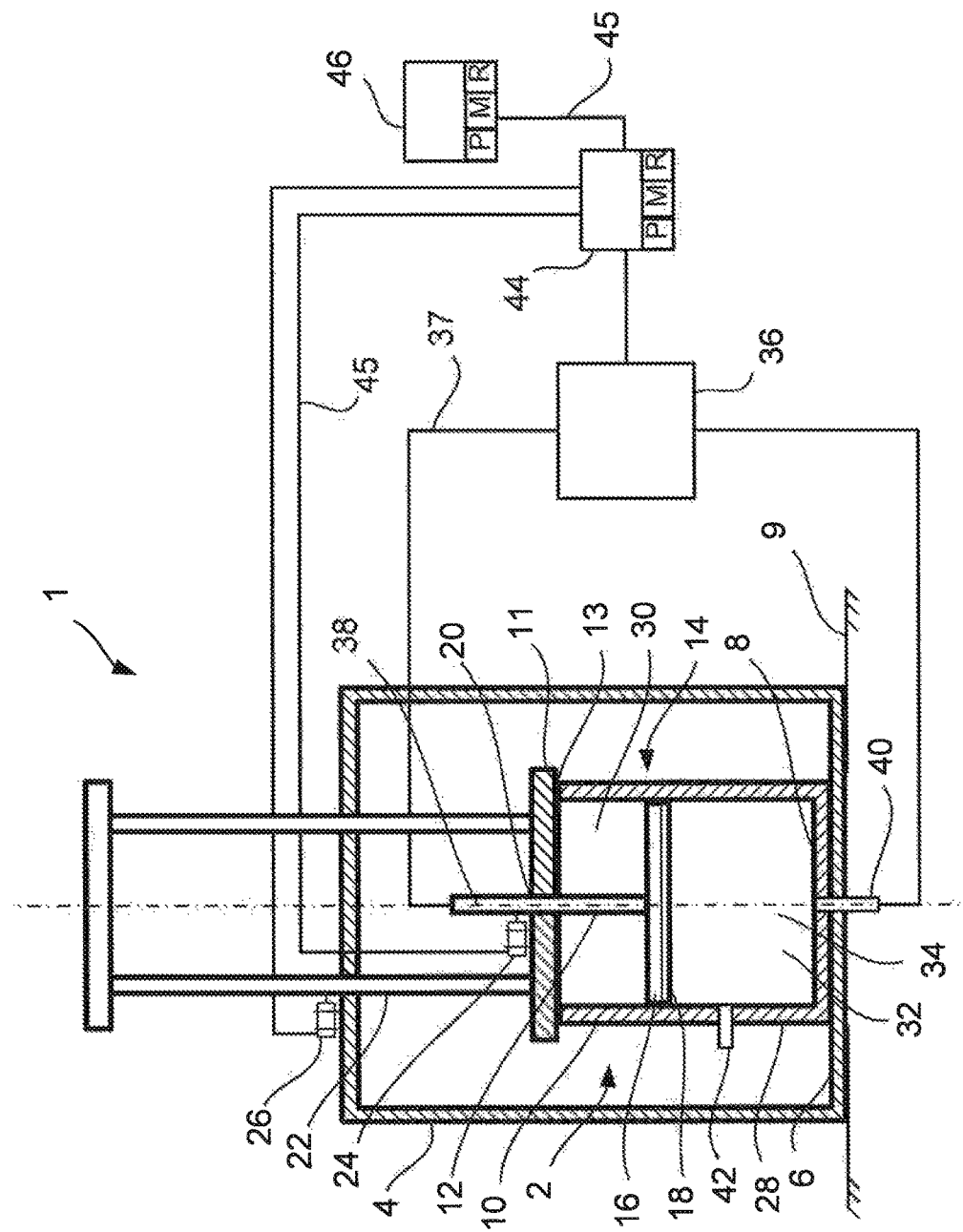
FIG. 1 shows a cross sectional view of an arrangement for a column according to an embodiment of the present invention.

FIG. 1 shows a cross sectional view of an arrangement 1 for a column 2 according to an embodiment of the present invention. The arrangement 1 comprising a stand 4 which is provided with a platform 6 adapted to receive a second end 8 or a bottom of a tubular housing 10 of the column 2 and for supporting the arrangement 1 on a floor 9. A first end unit 11 is removably connected to a first end 13 of the tubular housing 10. An adaptor rod 12 is connected to an adaptor assembly 14, which is movable within the tubular housing 10. The adaptor assembly 14 comprises a distributor plate 16 and a porous, perforated filter 18, which is arranged on the distributor plate 16. The adaptor rod 12 is arranged to extend through an opening 20 in the first end unit 11. A frame 22 is connected to the first end unit 11, which frame 22 and first end unit 11 can be lifted and lowered in a substantially vertical direction, so that the tubular housing 10 may be removed and substituted for another tubular housing 10' with different dimensions in relation to the removed tubular housing 10 when the frame 22 and first end unit 11 are lifted. More particularly, the first end unit 11 is adapted to be connectable to different tubular housings 10 with different diameters. The adaptor rod 12 is removably connected to the adaptor assembly 14, so that the adaptor assembly 14 may be removed and substituted for another adaptor assembly 14' adapted to the substituted tubular housing 10'.

In an embodiment, the tubular housing 10 has a cylindrical cross section. However, it is possible to provide the tubular housing 10 with another cross section, for example with a square cross section. The adaptor assembly 14 has a form which coincides with the form of the tubular housing 10.

A first actuating means 24 is arranged to lift and lower the adaptor rod 12 in a substantially vertical direction in relation to the first end unit 11. More particularly, the first actuating means 24 is a first electrical motor. However, the first actuating means 24 may also be a pneumatic or hydraulic cylinder.

A second actuating means 26 is arranged to lift and lower the frame 22. More particularly, the second actuating means 26 is a second electrical motor. However, the second actuating means 26 may also be a pneumatic or hydraulic cylinder.

The wall 28 and the second end 8 or bottom of the tubular housing 10 together with the first end unit 11 form a fluid space 30 and bed space 32, which spaces 30, 32 both are fluid tight and are capable of withstanding high operating pressures.

The bed space 32 is defined by the wall 28 of the tubular housing 10, the bottom and the adaptor assembly 14 connected to the adaptor rod 12. The bed space 32 is filled with a bed of packing material 34, which is usually particulate in nature and comprises or consists of a porous medium.

A liquid pump 36 is connected to the adaptor rod 12 and to the tubular housing 10 by means of conduits or pipes 37. A liquid mobile phase is arranged to enter through an inlet at the end of the adaptor rod 12 and flows through a central channel 38 in the adaptor rod 12 and further to the adaptor assembly 14. The liquid mobile phase thereafter moves through the bed of packing material 34 and is finally removed via an outlet 40 in the bottom of the tubular housing 10. Typically, the packing material 34 enclosed in the column 2 as a packed bed is generally formed by consolidating a suspension of discrete particles, known as slurry that is pumped, poured or sucked into the column 2 from a bore or nozzle 42 located at the tubular housing 10.

The distributor plate 16 comprises channels (not disclosed) arranged in a pattern to substantially uniform distribute the liquid mobile phase over the plate 16. The distributor plate 16 is perforated with holes or openings (not disclosed) which lead the liquid mobile phase from the channels and uniformly into the packing material 34.

An electronic control unit 44 is connected to the first actuating means 24, to the second actuating means 26 and to the liquid pump 36, e.g. by means of electrical wires 45. The control unit 44 is arranged to control the first actuating means 24, the second actuating means 26 and the liquid pump 36. According to the disclosed embodiment another computer 46 may also be connected to the control unit 44, e.g. by electrical wires 45. The control unit 44 and the computer 46 are both provided with a computer program P stored in an executable way or compressed manner in a memory M and/or in a readable/writable memory R.

Figure 2:
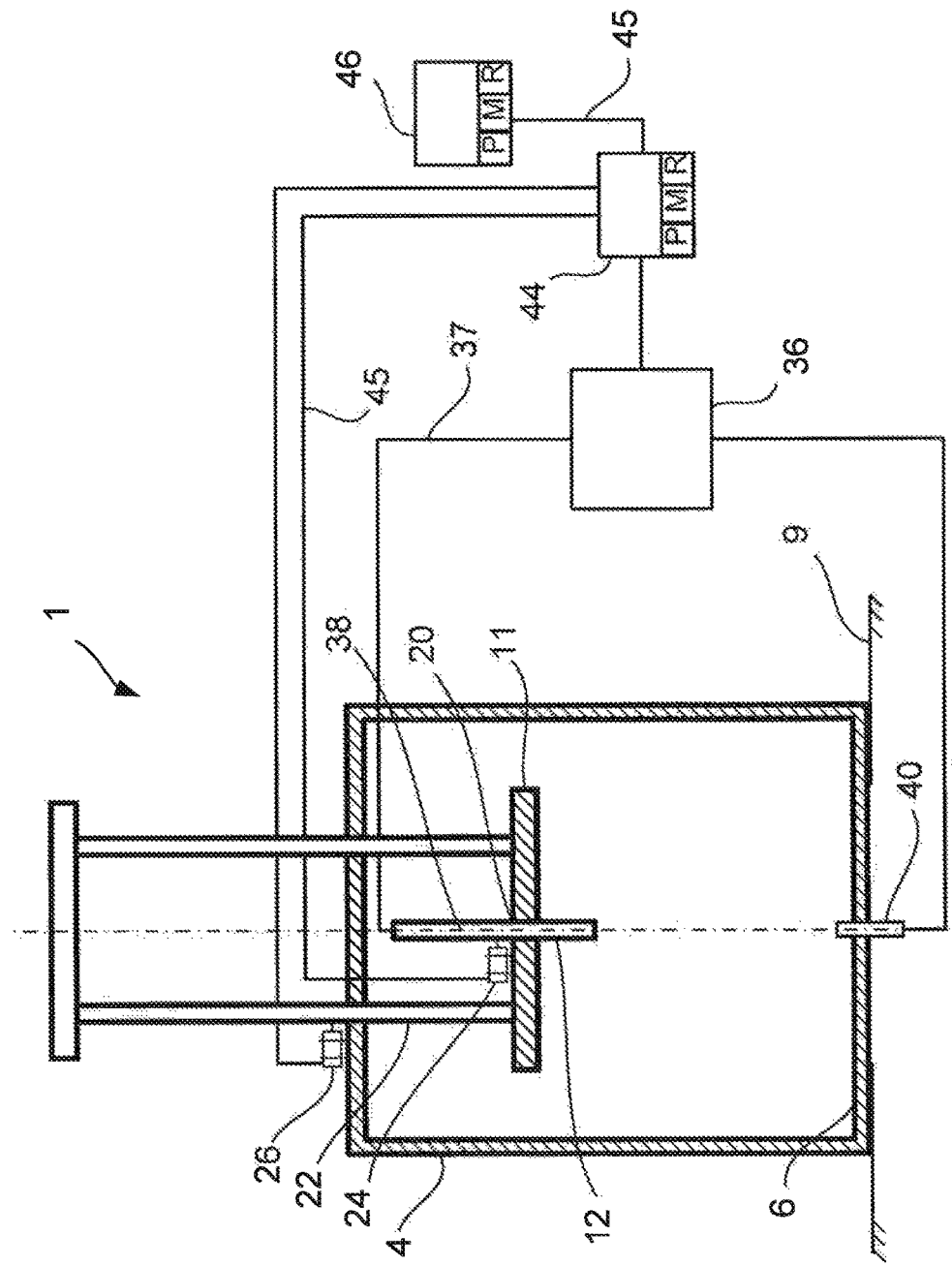
FIG. 2 shows a cross sectional view of the arrangement in FIG. 1 with a lifted upper end unit.

FIG. 2 shows a cross sectional view of the arrangement 1 in FIG. 1 with a lifted first end unit 11. The control unit 44 has instructed the second electrical motor 26 to lift the frame 22 and thereby also the first end unit 11. Also, the first electrical motor 24 has been instructed by the control unit 44 to lift adaptor rod 12 in relation to the first end unit 11. The tubular housing 10 and the adaptor assembly 14 have been removed from the arrangement 1.

Figure 3:
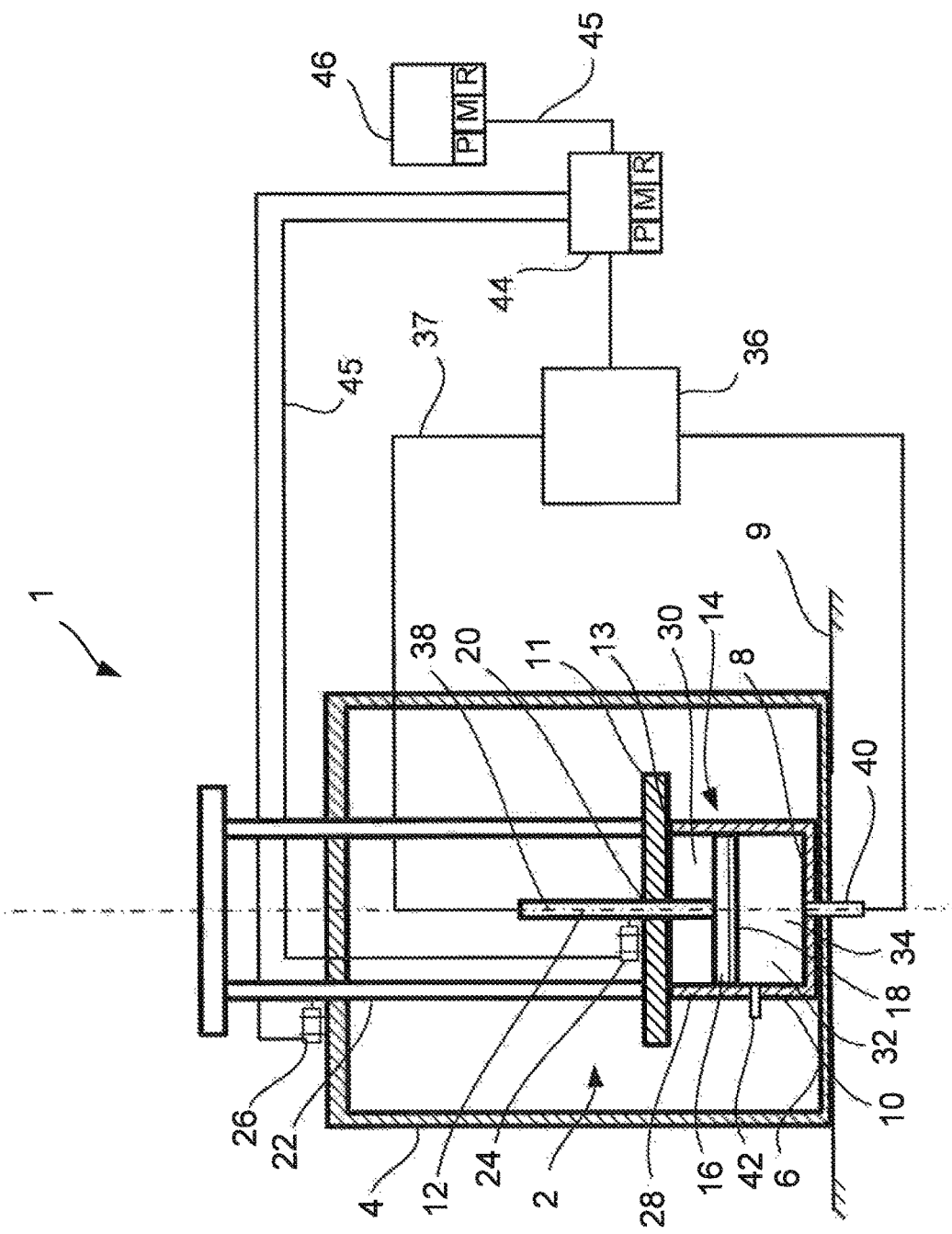
FIG. 3 shows a cross sectional view of the arrangement in FIG. 1 with a substituted column and adaptor assembly.

FIG. 3 shows a cross sectional view of the arrangement 1 in FIG. 1 with a substituted tubular housing 10' and adaptor assembly 14'. Both first and second electrical motors 24, 26 have been instructed by the control unit 44 to lower the frame 22 and the adaptor rod 12, so that the first end unit 11 has been connected to the first end 13 of the tubular housing 10. The new tubular housing 10' has a diameter and height which are smaller in size than the previous tubular housing 10. A wide range of column 2 capacities is possible, typically ranging from 0.1 to 2000 liters.

More particularly, column 2 is adapted for peptide and/or oligonucleotide synthesis. However, the arrangement 1 according to an embodiment of the invention can be used as a chromatography column.

Figure 4:
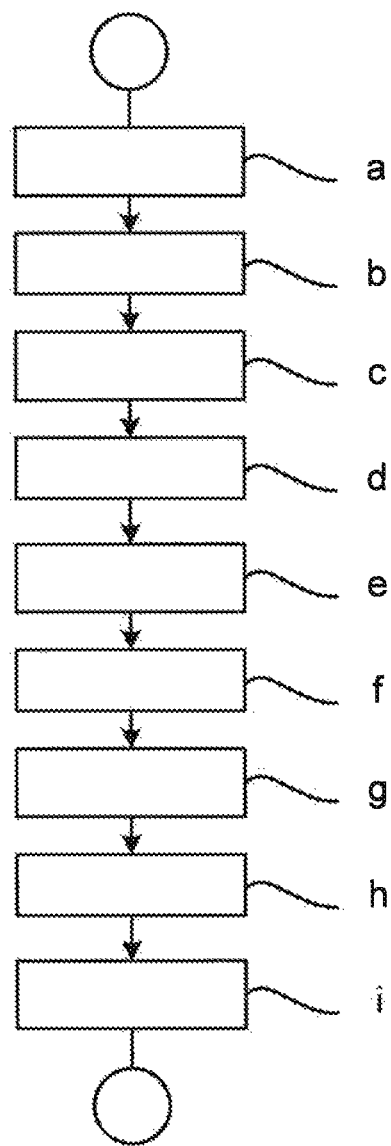
FIG. 4 shows a block scheme of the method for substituting the tubular housing in the arrangement for the column according to an embodiment of the present invention.

FIG. 4 shows a block scheme of the method for substituting the tubular housing 10 in the arrangement 1 for the column 2 according to an embodiment of the present invention. The method comprising the steps of: providing the stand 4 comprising the platform 6 adapted to receiving the second end 8 of a tubular housing 10 and for supporting the arrangement 1 on the floor 9; removably connecting the first end unit 11 to the first end 13 of the tubular housing 10; movably arranging the adaptor assembly 14 within the tubular housing 10; connecting the adaptor rod 12 to the adaptor assembly 14; and arranging the adaptor rod 12 to extend through the opening 20 in the first end unit 11.

The method comprising the further steps of: connecting the frame 22 to the first end unit 11; lifting the frame 22 and the first end unit 11 in a substantially vertical direction; removing the tubular housing 10 and substituting it for another tubular housing 10' with different dimensions in relation to the removed tubular housing 10; and lowering the frame 22 and first end unit 11 in a substantially vertical direction.

FIGS. 5A-5E show cross sectional views of a column 2 with an adaptor rod 12 and adaptor assembly 14 in different positions when performing a method of conducting peptide and/or oligonucleotide synthesis in the column 2. An oligonucleotide is a macromolecule comprising a sequence of nucleosides, each of which includes a sugar and a base. Each nucleoside is separated from adjacent nucleosides with an internucleoside linkage, which effectively serves to bond the nucleosides together. A number of different sugars and bases can be used. The internucleoside linkage is most commonly a phosphate, which may be substituted with a variety of substitutents at a non-bridging oxygen atom.

An even distribution of reagents makes it possible to minimize the dilution of the reagents and also to minimize the usage of expensive solvents. Applying reagents simultaneously over the cross sectional area of the packed bed is thus important for the result of the synthesis. Without a simultaneous introduction of fluid in the plane defined by the top of the packing material 34, it is virtually impossible to achieve so-called plug-flow behavior, which is a uniform and well-defined movement of the reagents through the packed bed and column 2, respectively, resulting in a uniform residence time distribution and thus minimizing the dilution of the reagents.

The method used for synthesizing peptides and oligonucleotides according to an embodiment of the present invention comprises a plurality of steps. To produce a large number of oligonucleotide molecules with this method, the packing material 34 is provided in the column 2 and a large number of DMT-protected nucleosides are fixed to the support.

Figure 5:
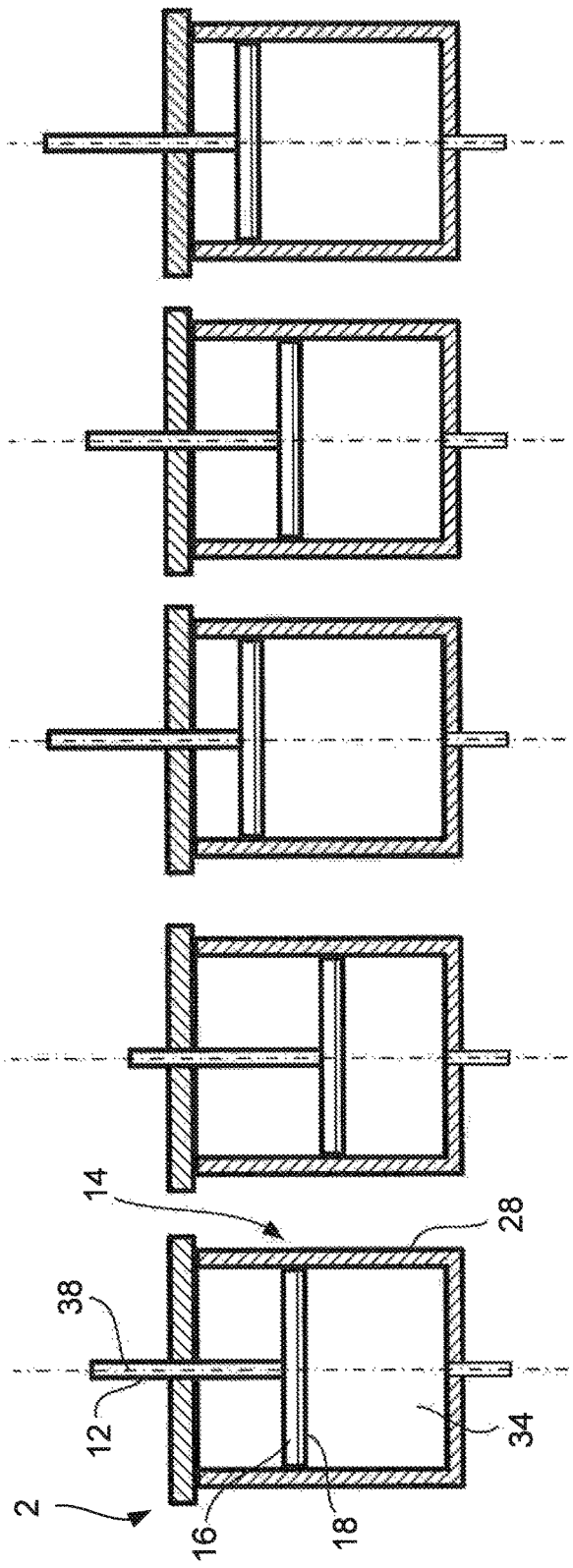
FIGS. 5A, 5B, 5C, 5D and 5E show cross sectional views of a column with and adaptor assembly in different positions.

FIG. 5A shows a first detritylation step where a deprotectant acting through a detritylation mechanism, is added to remove the DMT from nucleoside, and thus to "deprotect" that one hydroxyl. As a result, the last nucleoside in the sequence has one hydroxyl that is ready to receive a next amidite. Due to the product is building up on the media the volume of packing material 34 increases during the synthesis, partly due to swelling of the packing material 34 and partly due to swelling of the synthesized product. In an embodiment, column 2 is packed with packing material 34 about 50%-60% of total volume of the column 2, and for example with the concentration of: 111 mg/ml. The adaptor assembly 14 is positioned above the surface of and in contact with the packing material 34. This step is may be performed in toluene as a deprotectant.

FIG. 5B shows a second coupling step where nucleoside phosphoramidites, hereafter mentioned as "amidites", dissolved in a solvent such as acetonitrile, ACN, are introduced into the vessel. An activator, is also introduced into the vessel with the amidites. The phosphorus in the amidites bonds with the oxygen in the hydroxyl, thus providing support-bound nucleotides. After the support-bound nucleotides are formed, excess amidites are flushed from the vessel with acetonitrile. Since the packing material 34 contracts in acetonitrile the adaptor assembly 14 is automatically lowered, for example by 3%-4% in the coupling step. The length the adaptor assembly 14 is automatically lowered depends on the characteristics and the volume of the packing material 34 and also the dimensions of the tubular housing 10.

FIG. 5C shows a third oxidation step where an oxidizing agent is added to convert the trivalent phosphorous to pentavalent. Since the packing material 34 swells in the oxidation step the adaptor assembly 14 is automatically raised by 3%-4% in relation to the level in the first detritylation step.

After the oxidizing agent is flushed, a capping agent is added in a fourth capping step disclosed in FIG. 5D to block all the unprotected hydroxyls from reacting with amidites introduced at a later stage. The adaptor assembly 14 is automatically lowered to rest on the surface of the packing material 34, which corresponds to the level in the first detritylation step. Thereafter, acetonitrile again is introduced to flush out the capping agent.

The product is built on the packing material 34 and this causes an increased volume of the product and the packing material 34 in the each of the first step of each cycle up to approximate cycle number twelve. After this the product and the packing material 34 is relatively stable and the increase of volume is very small. FIG. 5E shows the process after the support is stable. For each cycle the adaptor assembly 14 is starting on a level which is 3%-4% higher than the level of the first step in the previous step in order to compensate for the swelling of the product and packing material 34.

Figure 6:
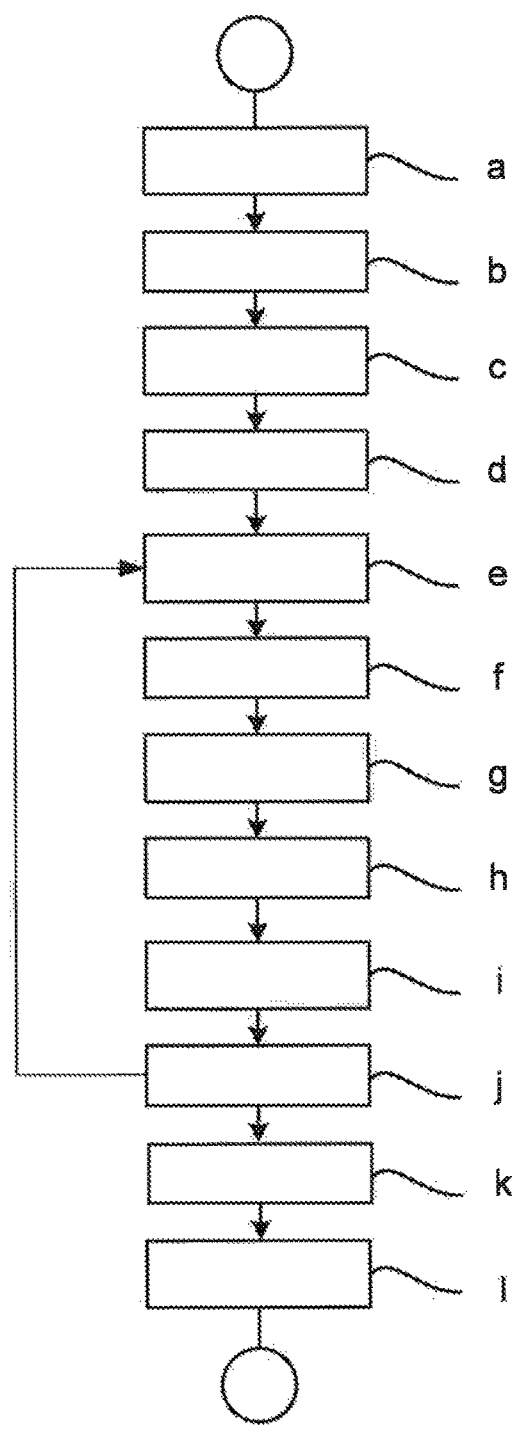
FIG. 6 shows a block scheme of a method for conducting peptide and/or oligonucleotide synthesis according to an embodiment of the present invention.

FIG. 6 shows a block scheme of the method for conducting peptide and/or oligonucleotide synthesis according to an embodiment of the present invention. The method comprising the steps of: providing a column 2 comprising; a tubular housing 10; a first end unit 11 connected to a first end of the tubular housing 10; an adaptor assembly 14 movable within the tubular housing 10; an adaptor rod 12 connected to the adaptor assembly 14, which adaptor rod 12 is arranged to extend through an opening in the first end unit 11; and automatically lifting and lowering the adaptor assembly 14 within the tubular housing 10 when conducting the peptide and/or oligonucleotide synthesis.

The method comprising the further steps of providing a packing material 34 below the adaptor assembly 14 in the tubular housing 10 and fix a number of protected nucleosides to the packing material 34; introducing a deprotectant into the tubular housing 10, which deprotectant acting through a detritylation mechanism for removing a protection group from the deprotectant; introducing aminoacid/amidite into the tubular housing 10; and lowering the adaptor assembly 14 within the tubular housing 10 introducing an oxidizing agent into the tubular housing 10; lifting the adaptor assembly 14 within the tubular housing 10; introducing a capping agent into the tubular housing 10; lowering the adaptor assembly 14 within the tubular housing 10; lowering and rising the adaptor assembly 14 within the tubular housing 10 by means of a first actuating means 24; and repeating the above-mentioned steps and lifting the adaptor assembly 14 within the tubular housing 10 before performing introducing aminoacid/amidite into the tubular housing 10.

In an embodiment, the deprotectant, the aminoacid/amidite in, the oxidizing agent and the capping agent are introduced through the channel 38 in the adaptor rod 12 and through the adaptor assembly 14. However, it is also possible to introduce these substances trough the outlet 40 in the bottom 8 of the tubular housing 10 and the substances will flow through the packed material 34 in the direction from the bottom 8 of the tubular housing 10 to the adaptor assembly 14. A second distributor plate (not disclosed) may be arranged at the bottom 8 of the tubular housing 10 to uniformly distribute the substances into the packing material 10.

According to an embodiment of the present invention there is arranged a computer program P, which comprises routines for controlling peptide and/or oligonucleotide synthesis in a column 2 according to an embodiment of the present invention.

The computer program P may comprise routines for controlling the liquid pump 36 which is connected to the adaptor rod 12 and to the tubular housing 10. When activating the liquid pump 36 the mobile phase with different substances according to above is arranged to enter through the inlet at the end of the adaptor rod 12 and to flow through the central channel 38 in the adaptor rod 12 and further to the adaptor assembly 14. The liquid mobile phase thereafter moves through the bed of packing material 34 and is finally removed via the outlet 40 in the bottom of the tubular housing 10 and back to the liquid pump 36.

The computer program P may comprise routines for controlling the first actuating means 24 arranged to lift and lower the adaptor rod 12 in a substantially vertical direction in relation to the first end unit 11. In an embodiment, the first actuating means 24 is the first electrical motor or may be a pneumatic or hydraulic cylinder. The length of movement of the adaptor assembly 14 depends on the characteristics and the volume of the packing material 34 and also the dimentions of the tubular housing 10. Based on experience the adaptor assembly 14 is arranged to move a distance suitable for compensating for the swelling of the packing material 34.

The computer program P may comprise routines for controlling the second actuating means 26 arranged to lift and lower the frame 22. In an embodiment, the second actuating means 26 is a second electrical motor or may be a pneumatic or hydraulic cylinder.

The program P may be stored in an executable way or compressed manner in the memory M and/or in the readable/writable memory R.

An embodiment of the present invention also relates to computer program product comprising a program code stored on a media readably by a computer 44, 46 for performing the method steps above, when the program code runs on an electronic control unit 44 or another computer 46 connected to the electronic control unit 44.

In all embodiments described above parts and surfaces being in contact with a process fluid are suitably selected from materials that are in accordance with typical material requirements in (bio-)pharmaceutical manufacturing or food grade quality. For example, materials are suitably in compliance with USP Class VI and 21 CFR 177. Furthermore they are suitably of animal-free origin and compliance to EMEA/41O/01.

Features and components of the different embodiments above may be combined within the scope of the invention.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An arrangement for a column comprising:
   a stand provided with a platform adapted to receive a second end of a tubular housing and for supporting the arrangement on a floor;
   a first end unit having a first end connected to a frame and an opposite second end removably connected to a first end of the tubular housing;
   an adaptor assembly movable within said tubular housing; and
   an adaptor rod connected to said adaptor assembly and arranged to extend through an opening in the first end unit; and
   wherein the frame together with the connected first end unit can be lifted and lowered in a substantially vertical direction relative to the stand where the tubular housing rests, so that the tubular housing may be removed and substituted for a substituted tubular housing with different dimensions in relation to the removed tubular housing when the frame and the first end unit are lifted.

2. The arrangement according to claim 1, wherein the adaptor rod is removably connected to said adaptor assembly, so that the adaptor assembly may be removed and substituted for another adaptor assembly adapted to the substituted tubular housing.

3. The arrangement according to claim 1, wherein the first end unit is adapted to be connectable to different tubular housings with different diameters.

4. The arrangement according to claim 1, wherein a first actuating means is arranged to lift and lower the adaptor rod in a substantially vertical direction in relation to the first end unit.

5. The arrangement according to claim 4, wherein the first actuating means is a first electrical motor.

6. The arrangement according to claim 1, wherein a second actuating means is arranged to lift and lower the frame.

7. The arrangement according to claim 6, wherein the second actuating means is a second electrical motor.

8. The arrangement according to claim 1, wherein a liquid pump is connected to the adaptor rod and to the tubular housing.

9. The arrangement according to claim 8, wherein a control unit is connected to a first actuating means arranged to lift and lower the adaptor rod in a substantially vertical direction in relation to the first end unit, to a second actuating means arranged to lift and lower the frame and to the liquid pump, which control unit is arranged to control the first actuating means, the second actuating means and the liquid pump.

10. The arrangement according to claim 1, wherein the column is adapted for peptide and/or oligonucleotide synthesis.

* * * * *